United States Patent [19]
Whitehead et al.

[11] Patent Number: 4,649,907
[45] Date of Patent: Mar. 17, 1987

[54] TRACTION SPLINT

[75] Inventors: David Whitehead, Kew; Graham Duell, Bentleigh; Donald Jordon, East Prahran, all of Australia

[73] Assignee: Australian Biomedical Corporation Limited, Australia

[21] Appl. No.: 706,677

[22] Filed: Feb. 28, 1985

[30] Foreign Application Priority Data

Feb. 29, 1984 [AU] Australia .................. PG3845

[51] Int. Cl.$^4$ ............................................. A61F 5/04
[52] U.S. Cl. .................................. 128/84 C; 128/85; 128/87 R
[58] Field of Search ............... 128/75, 80 R, 83, 84 R, 128/84 A, 84 C, 85, 87 R, 88; 73/172

[56] References Cited

U.S. PATENT DOCUMENTS

| 2,301,534 | 11/1942 | Goodwin | 128/84 R |
| 2,319,609 | 5/1943 | La Crosse | 128/84 R |
| 3,906,942 | 9/1975 | Lumb, Jr. et al. | 128/84 C |
| 3,942,521 | 3/1976 | Klippel | 128/85 |
| 4,265,230 | 5/1981 | Jordon | 128/87 R |

FOREIGN PATENT DOCUMENTS 637821 8/1983 Switzerland ................ 128/87 R

Primary Examiner—Richard T. Stouffer
Attorney, Agent, or Firm—Stevens, Davis, Miller & Mosher

[57] ABSTRACT

A traction splint for attachment to a person's leg for example and having an elongate U-shape frame. The side arms of the frame are telescopic and an air pump is connected to the frame so as to be operable to cause simultaneous extension of the two arms. A foot retaining device is attached to the arms adjacent the base of the U and a thigh ring is releasably securable to the movable sections of the two arms so that extension or contraction of the arms causes variation in the distance between the thigh ring and the foot retaining device. The thigh ring is completely separable from the arms and retaining structure is operable to prevent that separation. Also, the thigh ring can be opened at one side to allow it to be moved laterally over a person's leg.

26 Claims, 14 Drawing Figures

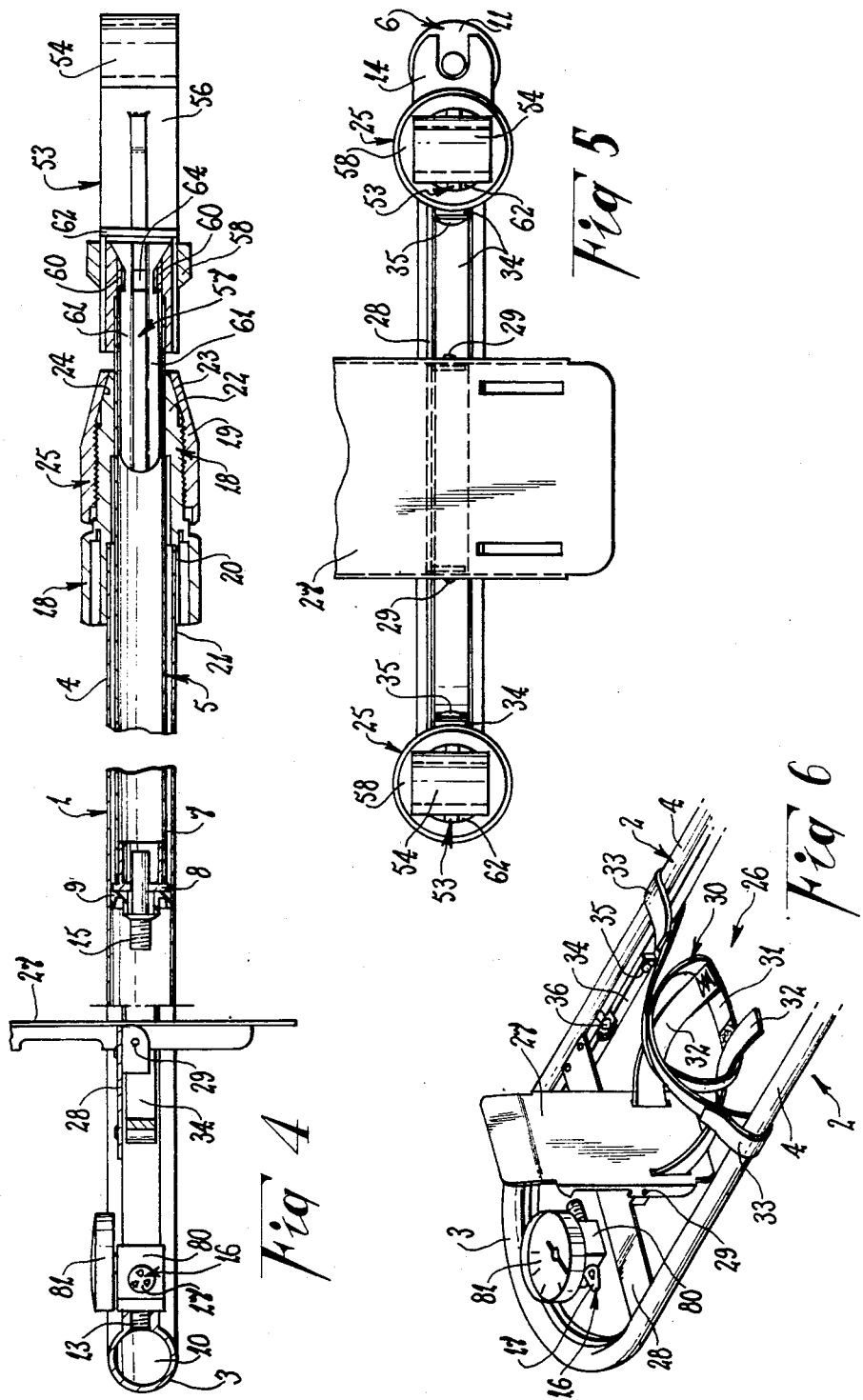

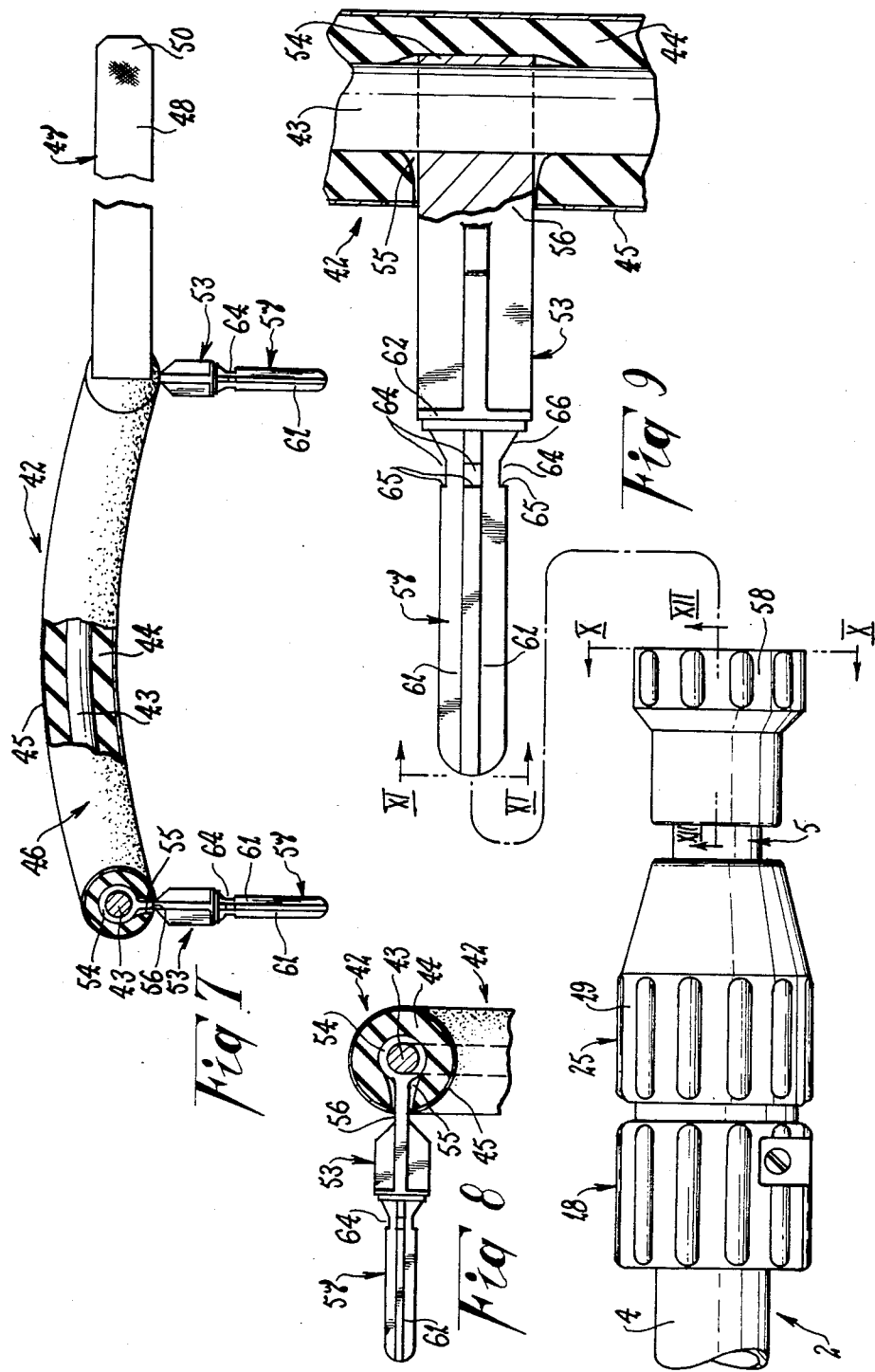

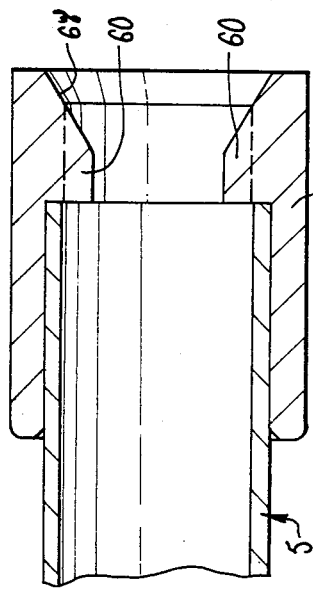
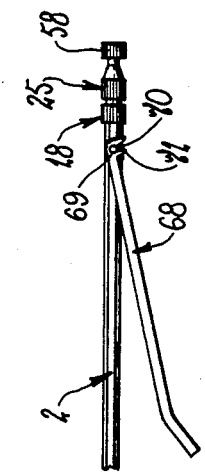
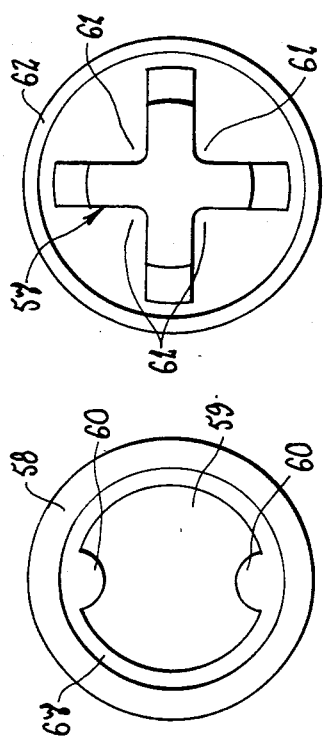
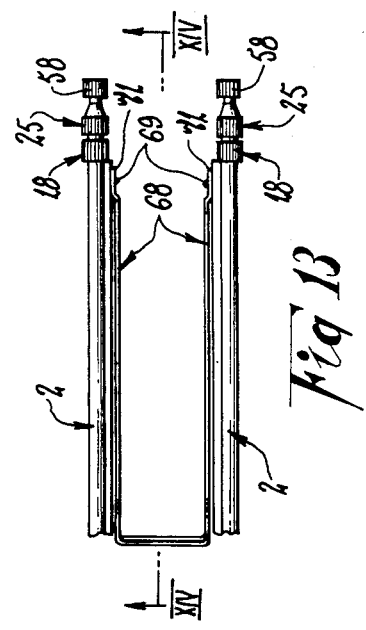

TRACTION SPLINT

This invention relates to traction splints of the kind used to keep the fractured bone parts of a broken limb in alignment and at the same time hold that limb under sufficient tension to ease the pain due to the fracture.

A traction splint of the foregoing kind forms the subject of U.S. Pat. No. 4,265,230. That prior splint has not been entirely satisfactory in use for a number of reasons. By way of example the method of attaching the caliper frame to the thigh ring does not have optimum effect and does not lend itself to speedy application of the splint. Furthermore, the method of extending the caliper and thereby applying tension to the broken limb is highly dependant on user skill to avoid discomfort to the accident victim because of sudden application of tension and/or application of excessive tension.

It is an object of the present invention to provide a traction splint of the foregoing kind which has an improved method of attaching the operative parts together and which is more convenient to use. Other objects and advantages of the invention will become apparent from the following description of one preferred form of the traction splint.

In accordance with one aspect of the present invention, there is provided a traction splint including, a caliper frame having two laterally spaced arms each of which is adjustable to enable variation of the length thereof, locking means for releasably securing each said arm against said length variation, retention means attached to said frame adjacent one end thereof and being attachable to a person's limb, an anchor member connected to the end of the frame opposite said one end thereof and being releasably securable around said limb, and releasable connecting means connecting said anchor member and said frame and being operable to either allow or prevent separation of said anchor member from said frame, the arrangement being such that adjustment of the length of said frame arms causes variation in the distance between said retention means and said anchor member.

According to a further aspect of the invention, there is provided a traction splint including a caliper frame having two laterally spaced arms, each said arm including two interconnected portions which are relatively adjustable to enable variation of the length of said arm, retention means attached to one part of each said arm and being attachable to a person's limb, an anchor member connected to the other said part of each said arm and being releasably securable around said limb, and pressure applying means which is operable to apply fluid pressure to at least one said part of each said arm so as to tend to cause extension of the length of said arms.

It is preferred that extension of the caliper is power assisted—e.g., through pneumatic, hydraulic, electrical, or mechanical means—so as to facilitate smooth application of tension. Adjustable tension limiting means may be also utilized to avoid excessive tensioning of the broken limb.

The essential features of the invention, and further optional features, are described in detail in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

In the drawings:

FIG. 4 is an enlarged cross sectional view taken along line IV—IV of FIG. 3, and in which some parts are omitted for convenience of illustration;

FIG. 5 is an end view of the splint shown in FIG. 4;

FIG. 6 is a perspective view of the foot holding means of the splint shown in FIG. 1;

FIG. 7 is a plan view of the thigh ring as shown in FIG. 1;

FIG. 8 is a cross sectional view taken along line VIII—VIII of FIG. 1;

FIG. 9 is a side elevation view of the connecting means between the thigh ring and the caliper, and which is shown in the separated condition;

FIG. 10 is a view taken along line X—X of FIG. 9;

FIG. 11 is a view taken along line XI—XI of FIG. 9;

FIG. 12 is across sectional view taken along line XII—XII of FIG. 9;

FIG. 13 is a plan view of part of the splint of FIG. 1 with a sub-frame attached; and FIG. 14 is a cross sectional view taken along line XIV—XIV of FIG. 13.

Figure 1:
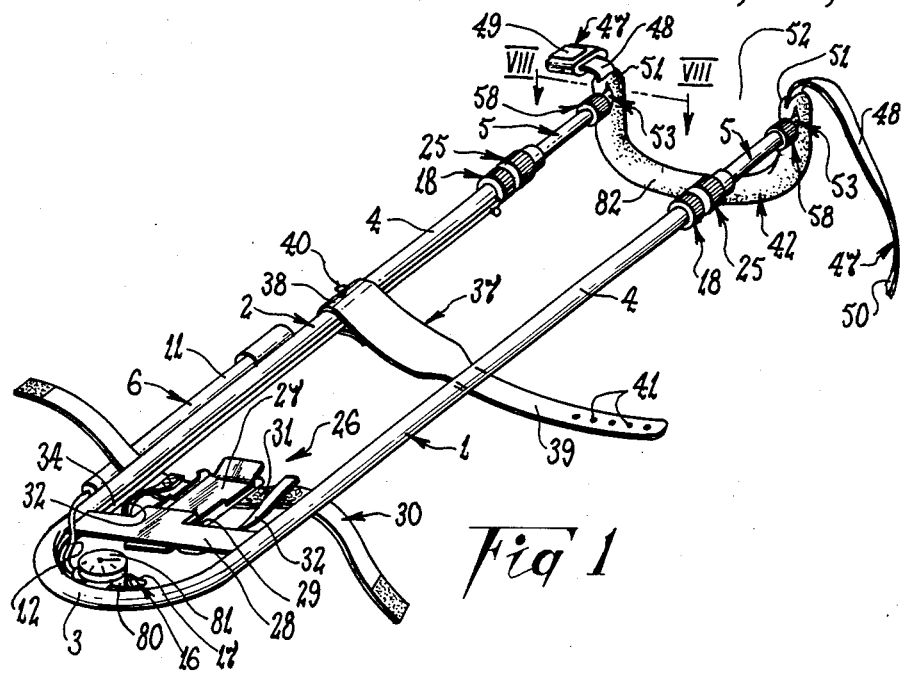
FIG. 1 is a perspective view of a traction splint according to one embodiment of the invention.

The caliper 1 is preferably in the form of a U-shaped frame having two laterally spaced arms 2 which are interconnected at one end through a curved bight portion 3. The arms 2 and bight portion 3 may be made of tubular aluminium or other suitable material and means is provided whereby the length of each arm 2 can be adjusted to alter the overall length of the caliper 1. In the arrangement shown, each arm 2 is composed of a main or tubular section 4 and a sliding section 5 which telescopes within the main section 4. According to the example shown, each main section 4 is formed integral with the bight portion 3 and the sliding section 5 is located remote from that portion 3.

Adjustment of the caliper length in the example shown is achieved through pneumatic means 6, but as indicated above other means may be used for that purpose. As best seen in FIG. 4, the innermost end portion 7 of each sliding section 5 may be arranged in the nature of a piston to be slidable within the larger diameter or main section 4 of the arm 2. Since the sliding section 5 is of tubular construction in the arrangement shown, the piston is formed by a cylindrical member 8 attached to the end portion 7 of that section 5 and a resilient sealing means 9 is provided around that member 8 to slidably engage the inner surface of the main section 4. Extension and contraction of the caliper is effected by introducing air into and removing air from respectively, the space 10 (FIG. 4) which exists between the two pistons 8,9.

In the arrangement shown, pressurized air is introduced into the air space 10 by means of a small hand pump 11 which may be similar to such pumps as used to inflate bicycle tires. Preferably, the pump 11 is attached to one arm 2 of the caliper 1 so as to be readily accessible for use and a flexible tube 12 of suitable form connects the pump outlet to an inlet port 13 of the air space 10. The inlet port 13 is located within the bight portion 3 in the arrangement shown, and the pump tube 12 connects with that port 13 through an adaptor 80 which carries a guage 81. In an alternative arrangement however, the adaptor 80 and guage 81 can be omitted so that the tube 12 connects direct to the bight portion 3. Any suitable clip means 14 may be provided to allow partial detachment of the pump 11 from the caliper 1 to enable convenient operation of the pump 11.

It is preferred that the guage 81 is calibrated so that it accurately shows the actual tension applied to a patient's leg in terms of force such as pounds force or kilogram force. That is, the calibration is such that allowance is made for the frictional and other forces which resist extension of the caliper 1 when the caliper 1 is not attached to a person's leg, and the guage 81 indicates the force which is actually being exerted by the caliper 1 at the particular pressure existing at that time within the air space 10.

A pressure relief valve 15 may be also provided on the caliper 1 so as to prevent excessive pressure being generated within the space 10 between the pistons 8,9. Preferably, that valve is adjustable to enable variation of the maximum pressure. In the construction shown, one such valve 15 is provided in each piston member 8 and air can escape from or enter the end of each sliding section 5 which is remote from the piston 8,9. Such a relief valve 15 may not be essential however, since the pump 11 and caliper 1 can be so arranged so to adequately limit the pressure which can be generated between the two pistons 8,9. Furthermore, the piston seals 9 may be arranged to allow escape of air if the pressure build-up is excessive.

Release of pressure to permit contraction of the caliper 1 may be effected tghrough a suitable manually operable bleed valve 16. If desired, that valve 16 may be constructed to also function as a relief valve as described above. In one arrangement, the valve 16 is constructed so that it can be set to open automatically when the pressure within the space 10 reaches a predetermined level, and a scale (not shown) may be associated with the valve 16 to enable convenient selection of a particular relief pressure. Such a valve 16 is also adapted for manual operation at any time to release the pressure within the space 10, and that may be achieved by depressing the cap 17 which may be spring loaded to automatically return to a valve closing position.

Locking means 25 is provided to hold the caliper arms 2 in a selected position of extension or contraction. In the form shown, the locking means for each arm includes a collet 18 secured to the main section 4 of the arm 2 and being cooperable with a tubular nut 19 to be clamped around or released from the sliding section 5.

The collet 18 may be formed of a plastics material or other resilient material and has a mounting portion 20 which receives and is secured to an end portion 21 of the main section 4 of the respective caliper arm 2. The collet 18 also has a clamping portion 22 which projects beyond the end portion 21 and which may be split in the longitudinal direction to facilitate radial expansion and contraction. An outer surface 23 of the clamping portion 22 is tapered to cooperate with a corresponding internal taper 24 of the tubular nut 19 so that axial adjustment of the nut 19 controls expansion and contraction of the clamping portion 22. Such axial adjustment may be effected through cooperation of the nut 19 with an external thread provided on the mounting portion 20 of the collet 18.

It will be appreciated from the foregoing that release of the locking means 25 is necessary before the caliper 1 can be extended or contracted. Although any suitable locking means may be employed, the particular means described has the advantages of simplicity and effectiveness.

The use of pneumatic means 6 to control the extension and contraction is also preferred because of its simplicity and effectiveness, although other forms of power assistance such as hydraulic, electrical or mechanical, could be adopted in place of the pneumatic means.

Figure 2:
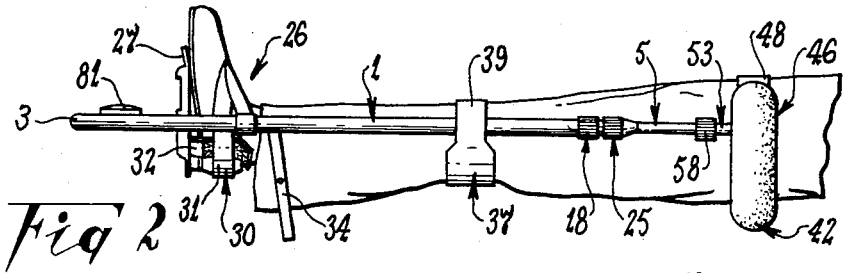
FIG. 2 is a side elevational view of the splint shown in FIG. 1 and shown attached to a persons leg.

Retention means 26 for attachment to a person's limb is provided on the caliper 1, and in the particular arrangement shown that means 26 is arranged for attachment to a person's foot and is located adjacent the bight portion 3. In the particular arrangement shown, the retention means 26 includes a foot plate 27 which is pivotally mounted on the caliper 1 for relative movement between an inoperative position as shown in FIG. 1 and an operative position as shown in FIG. 2. A mounting plate 28 is secured to the caliper 1 so as to extend between the arms 2 and the foot plate 27 is pivotally mounted at 29 on that mounting plate 28.

The retention means 26 also includes a strap assembly 30 which is attached to the foot plate 27 (FIG. 6). In the example shown, the assembly 30 has a support strap 31 which is adapted to bear against the rear of a person's foot or ankle region, a retainer strap 32 which connects the support strap 31 to the foot plate 27, and a pair of holding straps 33 which are arranged to be looped around the instep of the foot. Velcro (registered trade mark) fasteners or other devices may be used to releasably secure the strap 32 to the strap 31 so as to enable variation of the effective length of the strap 32. The particular assembly 30 shown in the drawings also includes extensions of the straps 33 which can be looped around respective caliper arms 2 and releasably secured thereto by Velcro (registered trade mark) or other fasteners so as to assist in holding the engaged foot against substantial sidewards movement. That assistance may not be necessary however, because of the attachment of the person's foot to the plate 27 and the inability of that plate 27 to move or swing laterally relative to the caliper arms 2.

It is also preferable to provide a stand 34 at the foot end of the caliper 1 which can be moved from a stowed position as shown in FIG. 1 to an operative position as shown in FIG. 2. In the example shown, the stand 34 is a "U" shaped member which is pivotally connected to each arm 2 at 35, and a snap engaging retainer 36 (FIG. 3) may function to releasably hold the stand 34 in the stowed position.

At least one leg support strap or plate 37 may be also provided on the caliper 1. Such a strap or plate 37 can take any suitable form, but in the arrangement shown it is a flexible strap which has one end portion 38 attached to one caliper arm 2 and has another portion 39 which is adapted to be looped around the other arm 2. The portion 39 can be releasably secured in the looped position by any suitable means such as by engaging a stud 40 provided at the end portion 38, within a selected one of a series of holes 41 provided in the portion 39.

An anchor member, which in the arrangement shown is in the form of a thigh ring 42 (FIGS. 1 and 2), is attachable to the caliper 1 through releasable connecting means as hereinafter described. As shown in FIGS. 1 and 7 the thigh ring 42 has an open mouth 52 at one side to enable the ring 42 to be passed laterally over a person's leg. Securing means as hereinafter described is provided on the thigh ring 42 to enable that ring 42 to be releasably secured around a person's leg.

In the particular construction shown, the thigh ring 42 is relatively rigid in that the body 46 of the ring 42 generally retains the U-shape configuration as shown in FIG. 1. There may be some degree of resilience in the body 46 to allow the lateral spacing of the mouth 52 to be increased or reduced, but the body 46 is otherwise form stable. The body 46 could be constructed in any suitable fashion, but in the arrangement shown by FIGS. 7, 8 and 9 it is composed of an elongate core section 43 of form stable material such as aluminium rod, a padding 44 of sponge rubber for example surounding the core section 43, and an outer covering 45 of fabric or other material surrounding the padding 44. Cooperable securing means 47 is attached to each end of the body 46 for releasably securing the ring 42 about a broken limb. The fabric or other material for the cover 45 is preferably selected so as not to have a capacity to irritate the patient.

Although the securing means 47 can take any of several forms, it is preferably composed of a length of webbing or strap 48 secured to each end of the body 46 and a buckle component 49 secured to one strap 48. The buckle component 49 is cooperable with an end portion 50 of the other strap 48 to releasably secure the two straps 48 together. Each strap 48 may be stitched or otherwise secured to end portions 51 of the cover 45 so as to effect attachment to the body 46 and those end portions 51 may extend beyond the respective adjacent ends of the core section 43 as shown to provide a flat and relatively flexible transition between the straps 48 and the core section 43. The effective length of the thigh ring 42 may be varied by adjusting the position of the buckle component along the length of its respective strap 48.

It is preferred that the ring 42 is arranged to follow as closely as possible the shape of the limb about which it is secured. In the case of the upper part of a leg, the back surface of that leg part will be relatively flat when the injured person is prone. Consequently, the ring 42 as shown is arranged to have a relatively flat and long base section 82 which will underly the leg back surface. In the example shown, the base section 82 has a slight curvature so that it extends upwardly towards each end and also extends towards the foot region of the caliper 1 (FIGS. 1 and 7).

Attachment of the caliper 1 and thigh ring 42 is effected through releasable connecting means which positively locks an end part of each caliper arm 2 to an adjacent part of the thigh ring 42. In one arrangement as shown in the drawings, the connecting means includes two locating pins 53, each of which is attached to the thigh ring 42 against separation and is cooperable with a respective one of the caliper arms 2.

Figure 3:
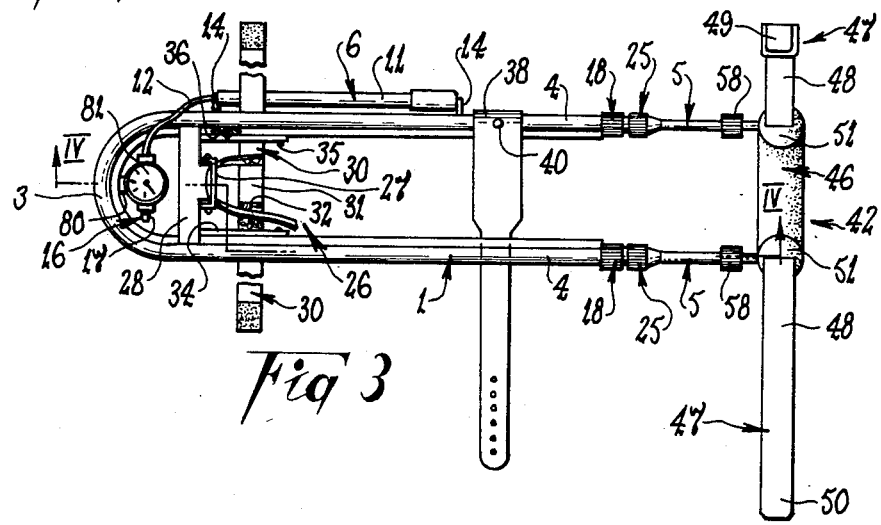
FIG. 3 is a plan view of the splint shown in FIG. 1.

FIGS. 4 and 5 show the pins 53 separated from the thigh ring body 46, whereas FIGS. 1 to 3 show them attached to the thigh ring body 46. The latter is the arrangement which will be adopted in actual practice.

In the particular arrangement shown, each pin 53 has a collar 54 at one end which slidably locates over the core section 43 of the thigh ring 42. The pin 53 is thereby secured against separation from the thigh ring 42 and, as shown by FIGS. 7 and 9, projects from the core section 43 through a slot 55 provided in one side of the ring body 46 so as to extend beyond that body 46 for engagement with the caliper 1. Each slot 55 may be of a length such as to permit lateral movement of the respective pin 53 so that the lateral spacing of the pins 53 can be varied to suit particular circumstances. As best seen in FIG. 4, each pin 53 has a relatively flat neck portion 56 which locates within the respective slot 55.

Each pin 53 has a projecting portion 57 which is adapted to be slidably located within the terminal end portion of the sliding section 5 of a respective one of the caliper arms 2 as shown in FIG. 4. Any suitable retaining means may be adopted to releasably secure the pin 53 against separation from the caliper arm 2, but in the arrangement shown that means comprises a bayonet-type connection. For that purpose, each sliding section 5 may have a collar 58 fixed to its terminal end portion against relative movement and the bore 59 of that collar 58 is provided with a plurality of projections 60 (FIG. 10). The projecting portion 57 of each pin 53 has a plurality of longitudinally extending grooves 61 (FIGS. 9 and 11), each of which can slidably receive a projection 60, and an enlargement 62 is provided on the pin 53 so as to limit its penetration into a sliding section 5. An undercut 64 (FIG. 9) is provided adjacent the enlargement 62 in order to form abutment shoulders 65 between adjacent grooves 61, and it is preferred that a tapered locating section 66 is provided between those shoulders 65 and the enlargement 62.

When a pin 53 is fully inserted into a sliding section 5 as shown in FIG. 4, the tapered section 66 of the pin 53 locates within a complementary tapered cavity 67 (FIG. 12) of the collar 58 and frictionally engages against the surface of that cavity 67. If the collar 58 and the respective sliding section 5 are then rotated relative to the pin 53, each of the projections 60 can be located behind a respective shoulder 65 and thereby prevent withdrawal of the pin 53 from the sliding section 5. Additional or reverse rotation will of course release the pin 53 for removal by placing each projection 60 in alignment with a respective groove 61.

It will be appreciated that, in the construction particularly described, the pins 53 are connected to the thigh ring 42 so as to be held against rotation about their respective longitudinal axes and that adds to the convenience of operating the aforementioned connecting means.

The caliper 1 may have means for attaching a sub-frame 68 (FIGS. 13 and 14) which, in hospital use, allows the splint to be adapted for leg exercise purposes. The sub-frame 68 may be pivotally attachable to the caliper arms 2 at any one of a plurality of positions adjacent the thigh ring 42 and extends away from that attachment generally towards the foot end. As shown, the pivotal attachment may include a pin 69 provided on each arm 2 and which is locatable within a slot 70 in an end 71 of a respective portion 72 of the sub-frame 68. Means (not shown) is provided on the sub-frame 68 to support the foot and lower part of the patient's leg. In use, the sub-frame pivot pin 69 is preferably located directly below the patient's knee so that the patient's leg can be exercised by up and down swinging movement of the sub-frame 68. Such movement may be facilitated by a cord (not shown) attached to the sub-frame 68 and passing over one or more pulleys (not shown) attached to the caliper 1 or other support.

In some respects, the traction splint herein described is similar to that described in U.S. Pat. No. 4,265,230 but advantages are derived from some changes to that prior construction. For example, the use of support straps rather than plates as in prior constructions, enables convenient movement of the support into and out of an operative position without requiring complete separation from the caliper.

Furthermore, the foot strap of the prior construction has the disadvantage that it does not resist rotation of the lower part of the injured person's leg. That fault is rectified in the arrangement herein described by provision of a foot plate and associated straps.

A significant advantage of the splint construction particularly described is that substantially equal tension is applied through each arm of the caliper when the splint is in use. That is, the interconnection of the interior of the two arms and use of fluid pressure within that interconnection ensures that the forces acting through the two arms are automatically balanced. As a result, application of the splint to a limb is simplified and the balance of tension between the two sides of the splint minimizes the possibility that the step of attaching the splint will cause discomfort to the injured person.

Yet another advantage of the splint is that it is adaptable to a wide range of age groups and body sizes.

Various alterations, modifications and/or additions may be introduced into the constructions and arrangements of parts previously described without departing from the spirit or ambit of the invention as defined by the appended claims.

Having now described our invention what we claim as new and desire to secure by Letters Patent is:

1. A traction splint including, a caliper frame having two laterally spaced arms each of which is adjustable to enable variation of the length thereof, locking means for releasably securing each said arm against said length variation, retention means attached to said frame adjacent one end thereof and being attachable to a person's limb, an anchor member connected to the end of said frame opposite said one end thereof and being releasably securable around said limb, and releasable connecting means connecting said anchor member and said frame and being operable to either allow or prevent separation of said anchor member from said frame, said connecting means including locating means on said anchor member which is cooperable with said frame arms to position said anchor member relative to said arms, and retaining means on each said frame arm which is operable to releasably hold said anchor member against separation from said frame, the arrangement being such that adjustment of the length of said frame arms causes variation in the distance between said retention means and said anchor member.

2. A traction splint according to claim 1, wherein each said arm is telescopic and includes a tubular section and a sliding section which is movable axially within the tubular section and extends beyond one end thereof, said tubular sections are interconnected at the ends thereof which are remote from their respective said one ends, and a said connecting means is associated with each said sliding section.

3. A traction splint according to claim 1, wherein extension means is operable to cause simultaneous extension of the two said arms.

4. A traction splint according to claim 2 wherein passage means interconnects the interiors of said tubular sections, pump means is operable to introduce fluid under pressure into said tubular sections, sealing means acts between each said sliding section and the respective said tubular section to substantially prevent escape of fluid, and release means is operable to permit escape of said fluid from said tubular sections.

5. A traction splint according to claim 1, wherein each said locating means includes a pin which is attached to said anchor member in laterally spaced relationship to the other said pin and which is insertable into an end of a respective said arm, and each said retaining means is operable to cooperate with the said pin of the respective said arm so as to hold said anchor member against separation from said frame.

6. A traction splint according to claim 5, wherein at least one abutment shoulder is formed on each said pin and arranged to face towards said anchor member, each said retaining means includes a collar attached to the respective said arm and having a projection formed thereon which is cooperable with a respective said abutment shoulder, and each said pin is insertable into the bore of a respective said collar and is restrained against removal therefrom when the relative rotational positions of said pin and collar is such that said projection and shoulder abut.

7. A traction splint according to claim 6, wherein each said pin is attached to the said anchor member so as to be held against rotation about its longitudinal axis relative to said anchor member, and each said collar is rotatably mounted on its respective said arm.

8. A traction splint according to claim 7, wherein each said arm is telescopic and includes a tubular section and a sliding section which is movable axially within the tubular section and extends beyond one end thereof, each said collar is secured to an end of a respective said sliding section, each said sliding section is rotatable about its longitudinal axis relative to the respective said tubular section, and said locking means is operative to secure the respective said sliding section against both longitudinal and rotational movement relative to the respective said tubular section.

9. A traction splint according to claim 1, wherein said retention means is adapted for engagement with a person's foot and includes strap means attached to said caliper frame so as to be located between the arms thereof at a position remote from said anchor member.

10. A traction splint according to claim 9, wherein said strap means includes side straps each of which is cooperable with a respective said arm so as to enable said retention means to restrain a person's foot against substantial turning movement towards either said arm.

11. A traction splint according to claim 9, wherein said retention means includes a plate pivotally mounted on said caliper frame for movement relative thereto between operative and inoperative positions.

12. A traction splint according to claim 1, wherein a stand is attached to said frame and is movable relative thereto to adopt an operative position at which it can engage a support surface and thereby hold in an elevated position the end of said frame which is remote from the anchor member.

13. A traction splint according to claim 1, wherein a sub-frame is pivotally attachable to said caliper frame and includes means for supporting a foot and lower part of a person's leg.

14. A traction splint according to claim 1, wherein at least one flexible leg support strap is attached to said caliper frame at a location between the ends thereof and so as to extend between said arms thereof.

15. A traction splint including a caliper frame having two laterally spaced arms, each said arm including two interconnected parts which are relatively adjustable to enable variation of the length of said arm, retention means attached to one said part of each said arm and being attachable to a person's limb, an anchor member connected to the other said part of each said arm and being releasably securable around said limb, and pressure applying means which is operable to apply fluid pressure to at least one said part of each said arm so as to tend to cause extension of the length of said arms.

16. A traction splint according to claim 15, including a gauge which is calibrated to compensate for frictional and other forces resisting extension of said arms when said splint is not attached to a person's limb.

17. A traction splint according to claim 16, wherein said gauge is calibrated to give a direct reading of the actual force tending to cause extension of said arms at a particular pressure being applied at that time by said pressure applying means.

18. A traction splint according to claim 15, wherein said arms are interconnected so that operation of said pressure applying means causes simultaneous extension of said arms.

19. A traction splint including, a caliper frame having two laterally spaced arms each of which is telescopically adjustable to enable variation of the length thereof, each said arm comprising a tubular section and sliding section which is movable axially within the tubular section and extends beyond one end thereof, the two said tubular sections being interconnected at the ends thereof which are remote from their respective said one ends, passage means interconnecting the interiors of the two said tubular sections, pump means operable to introduce fluid under pressure into said tubular sections, sealing means acting between each said sliding section and the respective said tubular section to substantially prevent escape of fluid, release means which is operable to permit escape of said fluid from said tubular sections, locking means for releasably securing each said arm against said length variation, retention means attached to said frame adjacent one end thereof and being attachable to a person's limb, an anchor member connected to the end of said frame opposite said one end thereof and being releasably securable around said limb, and releasable connecting means connecting said anchor member to each said frame arm and being operable to either allow or prevent separation of said anchor member from said arms, the arrangement being such that adjustment of the length of said frame arms causes variation in the distance between said retention means and said anchor member.

20. A traction splint according to claim 19, wherein relief means is connected to said tubular sections and is operable to prevent the pressure within said tubular sections exceeding a predetermined pressure.

21. A traction splint according to claim 20, wherein said relief means is adjustable to enable variation of said predetermined pressure.

22. A traction splint according to claim 20, wherein said sealing means forms or includes said relief means.

23. A traction splint according to claim 19, wherein said connecting means includes locating means on said anchor member which is cooperable with said frame arms to position said anchor member relative to said arms, and retaining means on each said frame arm which is operable to releasably hold said anchor member against separation from said frame.

24. A traction splint including, a caliper frame having two laterally spaced arms each of which is adjustable to enable variation of the length thereof, locking means for releasably securing each said arm against said length variation, retention means attached to said frame adjacent one end thereof and being attachable to a person's limb, an anchor member connected to the end of said frame opposite said one end thereof and being releasably securable around said limb, said anchor member including a body section formed of a rigid elongate core and a resilient padding provided around said core, said body section is of substantially "U" shape so as to have an open mouth at one side, releasable securing means is provided having two cooperable parts each of which is attached to said body section at a respective opposite side of said open mouth, said securing means being operable to retain said anchor member in ring-like form around a person's limb, and releasable connecting means connecting said anchor member and said frame and being operable to either allow or prevent separation of said anchor member from said frame, said connecting means including two locating pins provided on said anchor member in laterally spaced relationship and each of which is locatable within an end of a respective said arm, an open ended collar provided at one end of each said pin and arranged with its axis transverse to the longitudinal axis of the pin, and said core section passing through each said collar so as to hold the respective said pin against rotation about its longitudinal axis relative to said anchor member, the arrangement being such that adjustment of the length of said frame arms causes variation in the distance between said retention means and said anchor member.

25. A traction splint according to claim 24, wherein the effective length of said securing means is variable.

26. A traction splint according to claim 24 wherein each said pin projects through an opening provided through said padding, and at least one said opening is arranged so that the respective said pin is capable of limited movement along said core section whereby the lateral spacing between said pins can be varied.

* * * * *